(12) United States Patent
Kang et al.

(10) Patent No.: US 11,701,056 B2
(45) Date of Patent: Jul. 18, 2023

(54) EEG MEASURING DEVICE

(71) Applicants: IMEDISYNC, INC., Seoul (KR); EM-Tech. CO., LTD., Changwon-si (KR)

(72) Inventors: Seung Wan Kang, Seoul (KR); Tae-gyun Jeong, Seoul (KR); Jong Myung Kim, Suwon-si (KR); Bo Hyon Sim, Hwaseong-si (KR)

(73) Assignee: IMEDISYNC, INC. et al., Seoul (KR)

( * ) Notice: Subject to any disclaimer, the term of this patent is extended or adjusted under 35 U.S.C. 154(b) by 0 days.

(21) Appl. No.: 17/668,060

(22) Filed: Feb. 9, 2022

(65) Prior Publication Data

US 2022/0280109 A1  Sep. 8, 2022

(30) Foreign Application Priority Data

Feb. 10, 2021 (KR) .......................... 10-2021-0019519

(51) Int. Cl.
*A61B 5/00* (2006.01)
*A61B 5/369* (2021.01)

(52) U.S. Cl.
CPC ............ *A61B 5/6803* (2013.01); *A61B 5/369* (2021.01)

(58) Field of Classification Search
CPC ..... A61B 5/6803; A61B 5/0006; A61B 5/291; A61B 5/369; A61B 5/372; A61B 5/374; A61B 5/375; A61B 5/377; A61B 5/378; A61B 5/38; A61B 5/381; A61B 5/383
See application file for complete search history.

(56) References Cited

U.S. PATENT DOCUMENTS

| | | | | |
|---|---|---|---|---|
| 2005/0107716 A1* | 5/2005 | Eaton | ..................... | A61B 5/291 128/903 |
| 2009/0088619 A1* | 4/2009 | Turner | ................... | A61B 5/291 600/587 |
| 2009/0171181 A1* | 7/2009 | Kumada | ................ | A61B 5/291 600/383 |
| 2012/0143020 A1* | 6/2012 | Bordoley | .............. | A61B 5/1114 600/383 |
| 2014/0051044 A1* | 2/2014 | Badower | .............. | A61B 5/7203 434/236 |

FOREIGN PATENT DOCUMENTS

| | | |
|---|---|---|
| JP | 2001-340312 | 12/2001 |
| JP | 2006-43024 | 2/2006 |
| KR | 20080046969 A | 5/2008 |
| KR | 1020100077901 | 7/2010 |
| KR | 20160060535 A | 5/2016 |
| KR | 1020170011320 | 2/2017 |
| KR | 20170051699 A | 5/2017 |
| KR | 20180137756 A | 12/2018 |

(Continued)

OTHER PUBLICATIONS

Office Action in Korean Appln. No. 2021-0019519, dated Mar. 25, 2021, 10 pages (with English translation).

(Continued)

*Primary Examiner* — Etsub D Berhanu
(74) *Attorney, Agent, or Firm* — Fish & Richardson P.C.

(57) ABSTRACT

The present disclosure relates to an EEG measuring device which is in close contact with a head of a subject while having an adjustable size to fit the head of the subject.

10 Claims, 19 Drawing Sheets

(56) References Cited

FOREIGN PATENT DOCUMENTS

| | | |
|---|---|---|
| KR | 101987536 | 6/2019 |
| KR | 20200107302 A | 9/2020 |
| KR | 102293735 B1 | 8/2021 |

OTHER PUBLICATIONS

Decision to Grant in Korean Appln. No. 2021-0019519, dated Aug. 11, 2021, 4 pages (with English translation).
Decision to Grant in Korean Appln. No 10-2021-0109444, dated Nov. 20, 2021, 4 pages (with English Translation).
Decision to Grant in Korean Appln. No. 10-2021-0109445, dated Nov. 16, 2021, 4 pages (with English Translation).
Decision to Grant in Korean Appln. No. 10-2021-0109446, dated Nov. 14, 2021, 4 pages (with English Translation).
International Search Report in International Appln. No. PCT/KR2021/015418, dated Feb. 8, 2022, 7 pages (with English Translation).

* cited by examiner (b)

EEG MEASURING DEVICE

CROSS-REFERENCE TO RELATED APPLICATION

This application claims priority to and the benefit of Korean Patent Application No. 2021-0019519, filed on Feb. 10, 2021, the disclosure of which is incorporated herein by reference in its entirety.

TECHNICAL FIELD

The present disclosure relates to an electroencephalogram (EEG) measuring device, and more particularly, to an EEG measuring device which has an adjustable size to fit the heads of various subjects and can be in close contact with the heads of the subjects.

BACKGROUND

In general, various non-invasive measurement methods, such as an electroencephalogram (EEG), magnetoencephalography (MEG), and functional magnetic resonance imaging (fMRI), have been used to identify a functional mechanism of a brain.

Among these, the EEG is a set of electrical signals which measure a current flow inside a living body caused by the synchronized activity of nerve cells generated on a surface of a brain cortex using an electrode attached to a scalp. According to this EEG analysis, it is possible to non-invasively measure the activity information of cranial nerve cells.

Brain function research using the EEG has a variety of advantages such as a simpler measurement method compared to other brain function mapping methods, the least environmental constraints, an inexpensive system configuration, and excellent time resolution, and thus, the EEG is used as the most basic research tool in brain science and engineering research.

In recent years, various application technologies of the EEG are being studied and applied. That is, beyond a simple use for understanding an electrophysiological mechanism of a brain, the EEG is used to indirectly measure a person's cognitive, emotional or psychological state using machine learning and deep learning to diagnose various neuropsychiatric disorders such as Alzheimer's, anxiety disorders, schizophrenia, and depression, and is used in Neurofeedback in which a user learns how to regulate his/her EEG status to a desired EEG status while grasping their EEG status. Moreover, the EEG is used in a brain-computer interface (BCI) to manipulate an external device or assist communication using the EEG and used for therapeutic purposes by stimulating nerve cells in a brain using an electromagnetic field.

In this way, since the EEG is used in various research fields, a standard measurement method has been designated in the EEG; and this standard measurement method is called a 10-20 system. At least 19 electrode channels are required to record a reliable EEG; and it is recommended to use a larger number of channels if possible. In the montage of the 10-20 system, positions of the 19 electrodes mentioned above are designated based on a zone of the cerebral cortex.

The conventional EEG measuring system uses a wet electrode which minimizes an electrical impedance generated between a scalp and the electrode using a conductive gel. This is a factor which can cause considerable discomfort to an examinee (or subject), and has a disadvantage of having to wash his or her hair after an EEG examination.

As a solution to these disadvantages, an EEG measuring system using a dry electrode has emerged.

A dry EEG measurement uses a method of increasing conductivity by coating a conductive polymer. Unlike the wet electrode, there is a strong possibility that the scalp and the electrode are not in close contact. Accordingly, in order to solve the non-close contact therebetween, in general, a brush type electrode is used.

However, despite such efforts, it has not been able to overcome problems such as pain caused by the electrode brush, race, non-contact between the scalp and the electrode caused by differences in individual head shapes and head sizes, and non-contact between the scalp and the electrode caused by hair.

Therefore, in a dry electrode-based multi-channel EEG measuring device, there is a need to overcome the above-described problems.

SUMMARY

The present disclosure is directed to providing an EEG measuring device capable of efficiently measuring an EEG irrespective of differences in individual head shapes and head sizes.

The present disclosure is also directed to providing an EEG measuring device whose size can be changed according to differences in individual head shapes and head sizes.

The present disclosure is also directed to providing an EEG measuring device whose size can be variously changed according to a head size of a subject, particularly, the forehead and the back of the head of the subject.

The present disclosure is also directed to providing an EEG measuring device capable of recording a reliable EEG even if a size of the device is changed according to a head shape.

The present disclosure is also directed to providing an EEG measuring device which is in close contact with a head of a subject even if a size of the device is changed according to the head shape.

The problems to be solved by the present disclosure are not limited to the problems mentioned above, and other problems that are not mentioned will be clearly understood by those skilled in the art from the following description.

Particular implementations of the present disclosure provide an electroencephalogram (EEG) measuring device that includes a body, a sensor, a controller, and an adjuster. The body may be configured to be mounted at a head of a subject. The sensor may be provided at the body and configured to detect an electrical signal generated from the head. The controller may be configured to supply power to the sensor and convert the electrical signal detected by the sensor into an EEG signal. The adjuster may be provided at the body and configured to adjust a size of the body. The body may include a plurality of segments that are connected to each other and are movable relative to each other. The adjuster may be configured to bias each of the plurality of segments toward an adjacent segment of the plurality of segments.

In some implementations, the EEG measuring device can optionally include one or more of the following features. The body may include a side portion including a first side frame and a second side frame that is spaced apart from the first side frame and opposite to the first side frame, and a plurality of bridges connecting the first side frame to the second side frame. Each of the plurality of bridges may include a plurality of bridge housings, at least one movable housing connected to one or more of the plurality of bridge housings and configured to move with respect to one or more of the plurality of bridge housings, and a plurality of connection frames connecting one or more of the plurality of bridge housings to the side portion or connecting the plurality of bridge housings to the at least one movable housing. The adjuster may be provided at each of the plurality of bridge housings. The plurality of connection frames may include a first connection frame and a second connection frame. The adjuster may include an adjustment housing provided at one or more of the plurality of bridge housings, and a symmetrical mover provided inside the adjustment housing and configured to move the first connection frame and the second connection frame respectively. The first connection frame may be connected to a first end of the adjustment housing, and the second connection frame may be connected to a second end of the adjustment housing being opposite to the first end of the adjustment housing. The symmetrical mover may include a first connection rack gear connecting a first side of the adjustment housing to the first connection frame, a second connection rack gear connecting a second side of the adjustment housing to the second connection frame and being spaced apart from the first connection rack gear, and a connection pinion gear configured to engage with each of the first connection rack gear and the second connection rack gear. The first connection rack gear and the second connection rack gear may be positioned to face each other. The symmetrical mover may further include an adjustment elastic member coupled to the connection pinion gear and configured to, based on the connection pinion gear rotating in a first rotational direction, apply a restoring force to the connection pinion gear in a second rotational direction opposite to the first rotational direction. The adjuster may include a stopper configured to limit rotation of the connection pinion gear. The stopper may include a first protrusion configured to contact each of a surface of the first connection rack gear and a surface of the second connection rack gear, and a second protrusion configured to contact each of an opposite surface of the first connection rack gear and an opposite surface of the second connection rack gear. The plurality of bridge housings in one or more of the plurality of bridges may include a first bridge housing connected to the first side frame and a second bridge housing connected to the second side frame. The at least one movable housing in the one or more of the plurality of bridges may include a first movable housing connecting the first bridge housing to the second bridge housing. The plurality of bridge housings in one or more of the plurality of bridges may include a first bridge housing connected to the first side frame, a second bridge housing connected to the second side frame, and a third bridge housing. The at least one movable housing in the one or more of the plurality of bridges may include a first movable housing connecting the first bridge housing to the third bridge housing, and a second movable housing connecting the second bridge housing to the third bridge housing. The sensor may include a sensor housing having a first side and a second side. The first side may be coupled to an inner peripheral surface of the body. The second side may define an opening. The sensor may further include an electrode coupled to an inner side of the sensor housing and protruding through the opening, and an elastic member provided between the first side of the sensor housing and the electrode and configured to apply an elastic force to the electrode. The sensor may include a vibrator positioned between the electrode and the elastic member and configured to vibrate, and a light emitting diode (LED) positioned at the electrode and configured to emit infrared rays.

According to an aspect of the present disclosure, there is provided an EEG measuring device including: a body mounted on a head of a subject; a sensing unit provided in the body to detect an electrical signal generated from the head; a controller configured to supply power to the sensing unit and convert the electrical signal detected by the sensing unit into an EEG signal; and an adjuster provided in the body to adjust a size of the body, wherein the adjuster provides a restoring force to the body when the size of the body increases.

The body may include a side portion including a first side frame and a second side frame spaced apart from the first side frame and a plurality of bridges configured to connect the first side frame and the second side frame to each other, and the adjuster may be provided in the bridge.

The adjuster may include an adjustment housing and a symmetrical mover which is provided in the adjustment housing and moves the bridge closer to or away from the adjustment housing, and the bridge may include a connection frame configured to connect one side of the adjustment housing and any one of the first side frame and the second side frame to each other and connect the other side of the adjustment housing and the other of the first side frame and the second side frame to each other.

The symmetrical mover may include a first connection rack gear configured to connect one side of the adjustment housing and the connection frame to each other, a second connection rack gear configured to connect the other side of the adjustment housing and the connection frame to each other and provided to be spaced apart from the first connection rack gear, and a connection pinion gear provided to engage with each of the first connection rack gear and the second connection rack gear, the first connection rack gear and the second connection rack gear may move closer to each other when the connection pinion gear rotates in a forward direction, and the first connection rack gear and the second connection rack gear may move away from each other when the connection pinion gear rotates in a reverse direction.

The symmetrical mover may further include an adjustment elastic member which is coupled to the connection pinion gear and provides a restoring force to the connection pinion gear when the connection pinion gear rotates in the reverse direction so that the connection pinion gear rotates in the forward direction.

The adjuster may further include a stopper configured to limit the rotation of the connection pinion gear, the stopper may include a locking member provided on an end portion of the connection frame and a protruding member provided inside the adjustment housing to come into contact with the locking member, and the protruding member may include a first protruding member which limits the rotation of the connection pinion gear in the forward direction and a second protruding member which is provided farther from the connection pinion gear than the first protruding member and limits the rotation of the connection pinion gear in the reverse direction.

The adjustment housing may include a first first-type adjustment housing and a second first-type adjustment housing spaced apart from each other, the bridge may further include a first movable housing provided between the first first-type adjustment housing and the second first-type adjustment housing, and the connection frame may include a first first-type connection frame configured to connect any one of the first side frame and the second side frame and the first first-type adjustment housing to each other, a second first-type connection frame configured to connect the first first-type adjustment housing and second first-type adjustment housing to each other and pass through the first movable housing, and a third first-type connection frame configured to connect the second first-type adjustment housing and the other of the first side frame and the second side frame to each other.

The adjustment housing may include a first second-type adjustment housing, a second second-type adjustment housing, and a third second-type adjustment housing spaced apart from each other, the bridge may further include a first second-type movable housing provided between the first second-type adjustment housing and the second second-type adjustment housing and a second second-type movable housing provided between the second second-type adjustment housing and the third second-type adjustment housing, and the connection frame may include a first second-type connection frame configured to connect any one of the first side frame and the second side frame and the first second-type adjustment housing to each other, a second second-type connection frame configured to connect the first second-type adjustment housing and second second-type adjustment housing to each other and pass through the first second-type movable housing, a third second-type connection frame configured to connect the second second-type adjustment housing and the third second-type adjustment housing to each other and pass through the second second-type movable housing, and a fourth second-type connection frame configured to connect the third second-type adjustment housing and the other of the first side frame and the second side frame to each other.

The sensing unit may include a sensor housing of which one side is coupled to an inner peripheral surface of the body and the other side includes an opening, an electrode coupled to an inner side of the sensor housing to protrude through the opening, and an elastic member provided between the one side of the sensor housing and the electrode to provide an elastic force to the electrode.

The sensing unit may further include a vibrator provided between the electrode and the elastic member to vibrate, and an LED provided inside the electrode to emit infrared rays.

Other specific details of the present disclosure are included in the detailed description and drawings.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, an exemplary embodiment of the present disclosure will be described with reference to the drawings. The following detailed description is provided to aid in a comprehensive understanding of methods, devices and/or systems described herein. However, this is only an example and the present disclosure is not limited thereto.

In describing the exemplary embodiment of the present disclosure, when it is determined that a detailed description of known technologies related to the present disclosure may unnecessarily obscure a subject matter of the present disclosure, detailed descriptions thereof will be omitted. In addition, terms to be described later are terms defined in consideration of functions in the present disclosure, which may vary according to intention or custom of a user or an operator. Therefore, the definitions of the terms should be made based on the contents throughout the present specification. The terms used in the detailed description are only for describing the embodiments of the present disclosure, and should not be limiting. Unless explicitly used otherwise, expressions in the singular form include the meaning of the plural form. In the present description, expressions such as "comprising" or "including" are intended to refer to certain features, numbers, steps, operations, elements, some or combinations thereof, and the expressions are not to be construed to exclude the presence or possibility of one or more other features, numbers, steps, operations, elements, some or combinations thereof, other than those described.

Meanwhile, the term first, second, or the like is used to describe various elements or components, but these elements or components are, of course, not limited by these terms. These terms are only used to distinguish one element or component from another element or component. Therefore, it goes without saying that the first element or component mentioned below may be a second element or component within a technical idea of the present disclosure.

Unless otherwise defined, all terms (including technical and scientific terms) used in the present specification may be used as meanings that can be commonly understood by those of ordinary skill in the art to which the present disclosure belongs. In addition, terms defined in a commonly used dictionary are not interpreted ideally or excessively unless explicitly defined specifically.

Hereinafter, an overall configuration of an EEG measuring device 10 according to one exemplary embodiment of the present disclosure will be described with reference to FIGS. 1A to 2C.

Figure 1A:
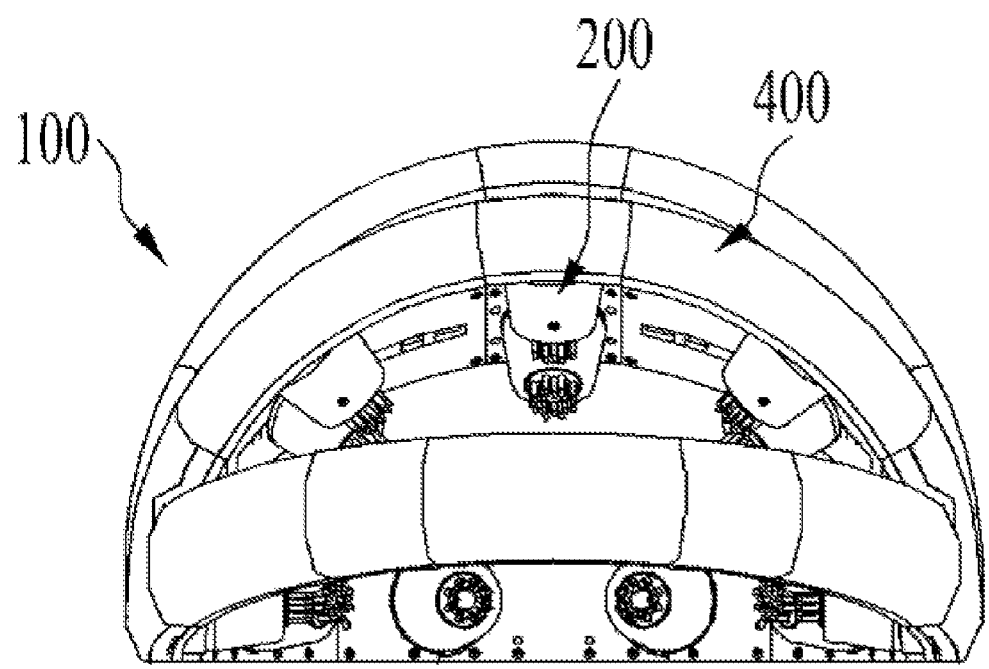
FIGS. 1A to 1C are views illustrating a case in which a size of an EEG measuring device according to one exemplary embodiment of the present disclosure is minimum.
Figure 1B:
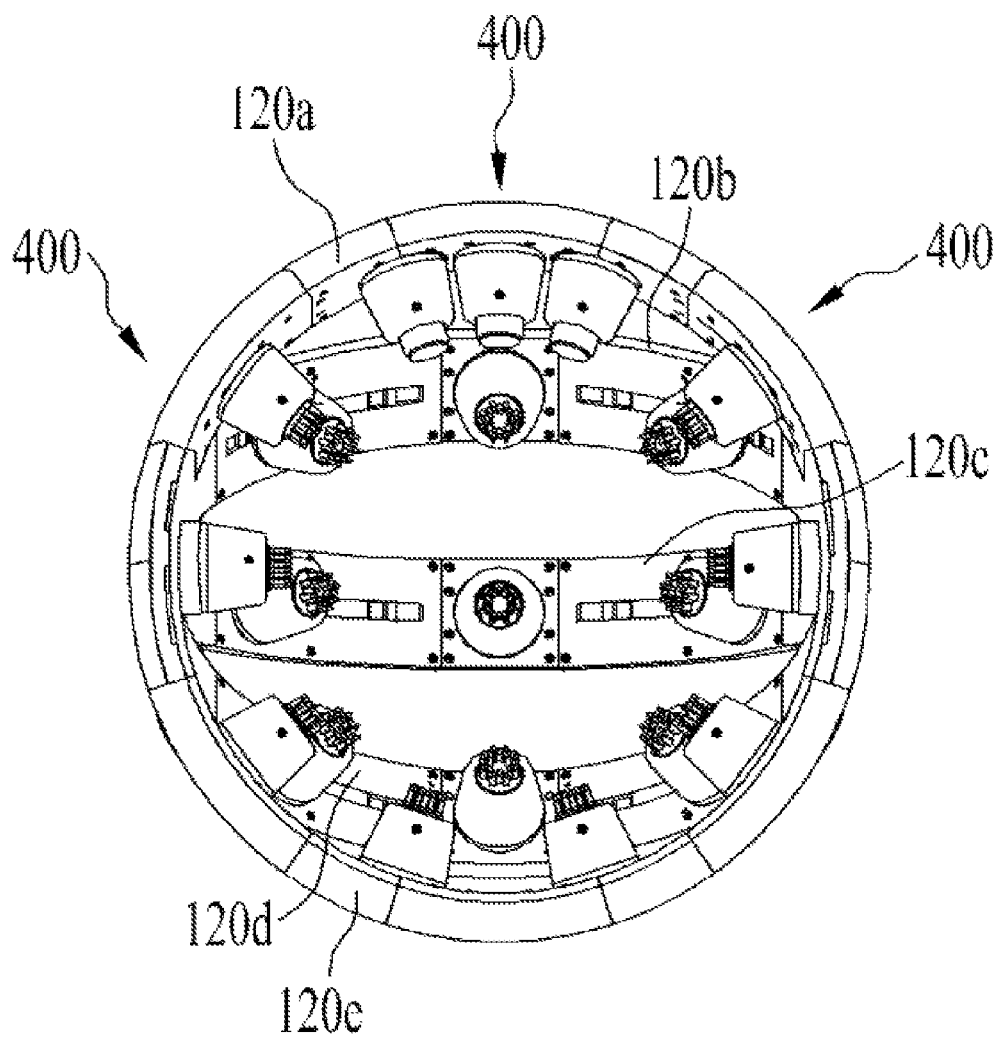
Figure 1C:
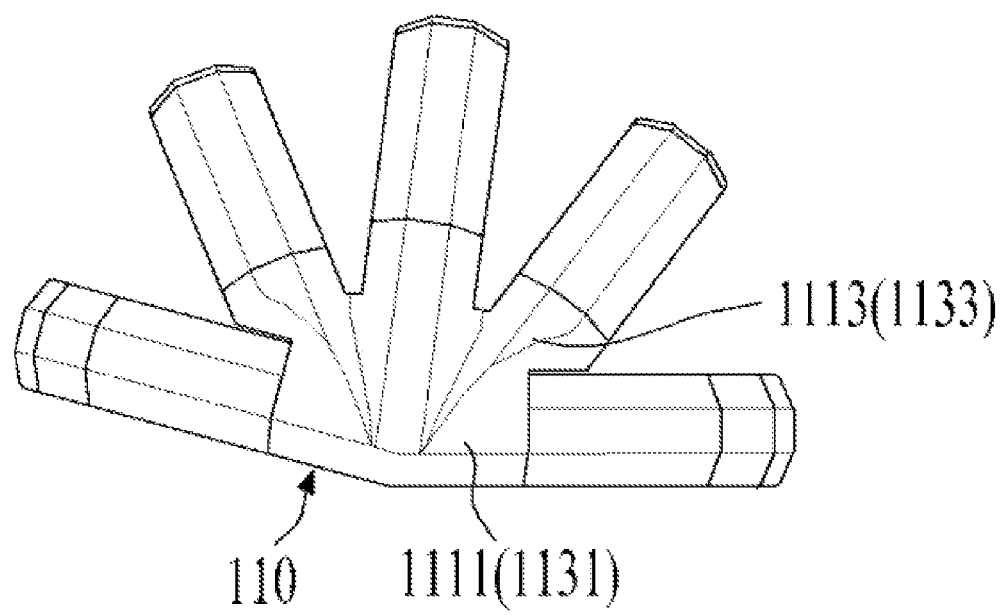

FIG. 1A is a view when the EEG measuring device 10 having the minimum size is viewed from the front, FIG. 1B is a view when the EEG measuring device 10 having the minimum size is viewed from below, and FIG. 1C is a view illustrating a side portion of the EEG measuring device 10 having the minimum size.

Figure 2A:
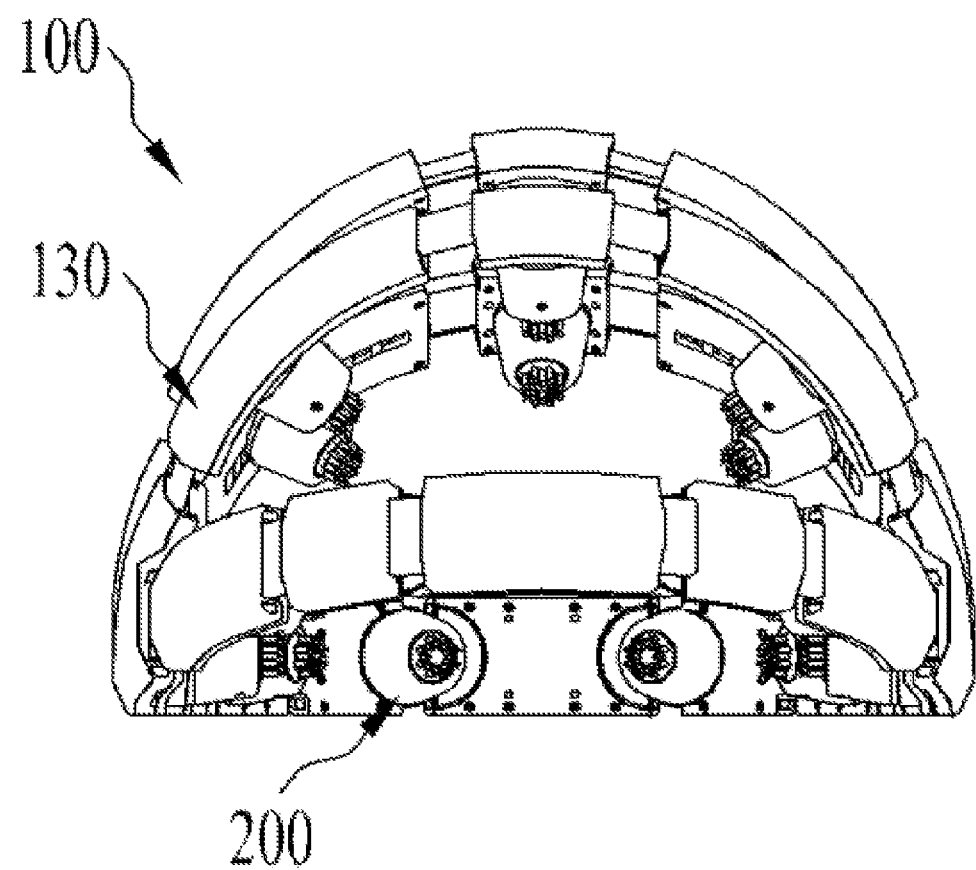
FIGS. 2A to 2C are views illustrating a case in which the size of the EEG measuring device according to one exemplary embodiment of the present disclosure is maximum.
Figure 2B:
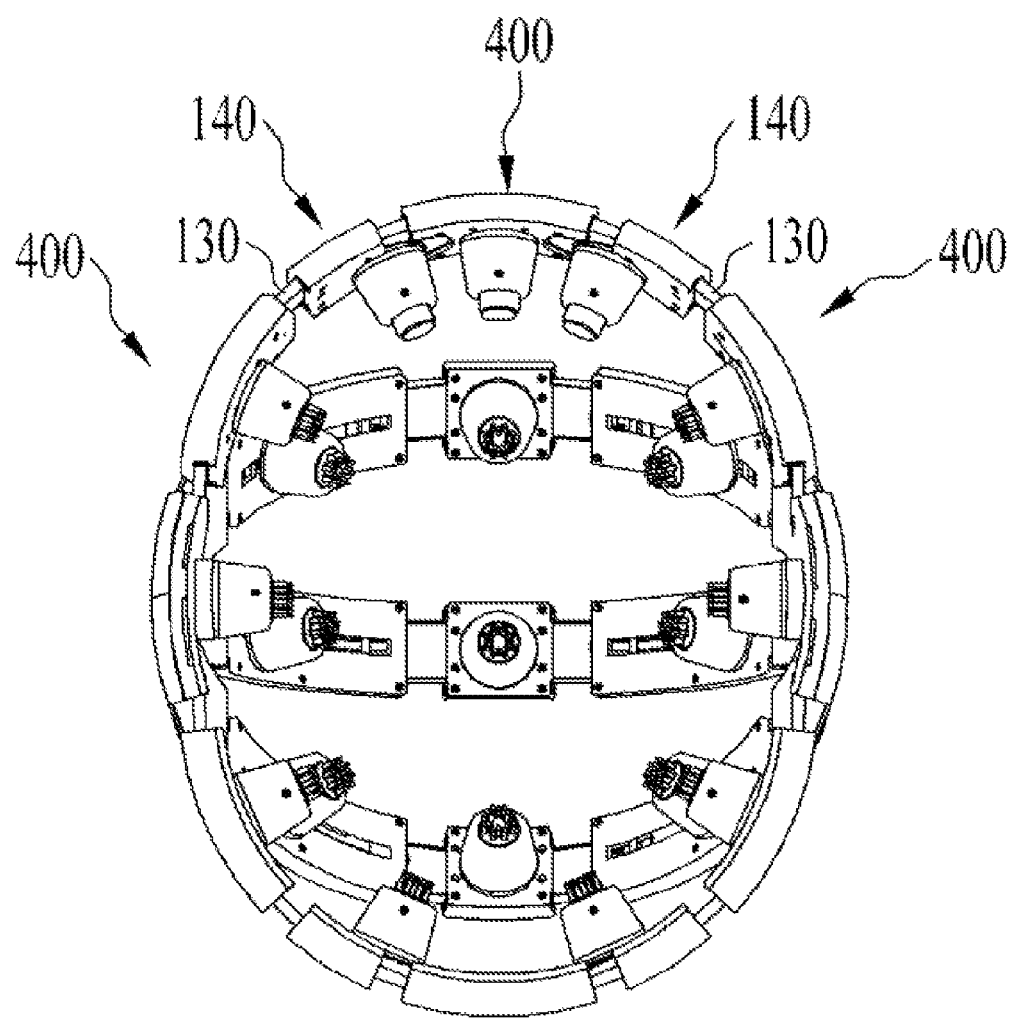
Figure 2C:
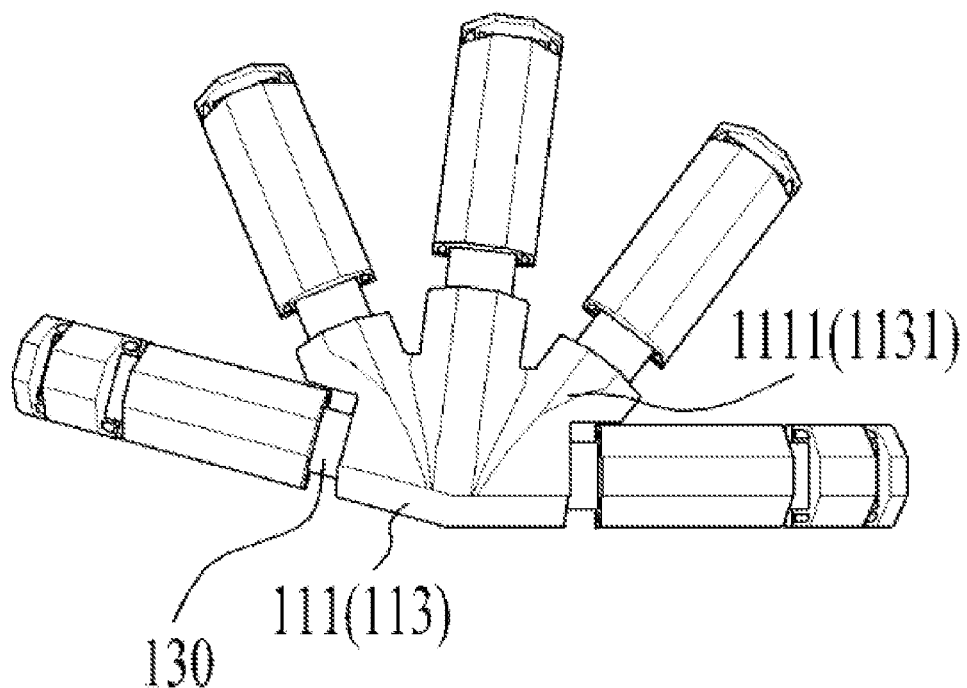

FIG. 2A is a view when the EEG measuring device 10 having the maximum size is viewed from the front, FIG. 2B is a view when the EEG measuring device 10 having the maximum size is viewed from below, and FIG. 2C is a view illustrating the side portion of the EEG measuring device 10 having the maximum size.

The EEG measuring device 10 according to one exemplary embodiment of the present disclosure includes a body 100 which is mounted on a head of a subject, a sensing unit 200 which is provided in the body 100 to detect an electrical signal generated from the head of the subject, a controller 300 which supplies power to the sensing unit 200 and converts the electrical signal detected by the sensing unit 200 into an EEG signal, and an adjuster 400 which is provided in the body 100 to adjust a size of the body 100.

When the size of the body 100 increases, the adjuster 400 may provide a restoring force to the body 100 so that the body 100 can be returned to a size before the size of the body 100 increases, and this will be described later in detail in FIGS. 7A and 7B. The increase in the size of the body 100 may mean that a distance between a plurality of components constituting the body increases. In addition, the increase in the size of the body 100 may mean a state in which a component connected to the adjuster 400 among the components constituting the body moves relative to the adjuster 400 and is away from the adjuster 400.

The body 100 according to the exemplary embodiment of the present disclosure may be provided in a shape to be mounted on the head of the subject, and may be provided to cover at least a portion of the head of the subject.

To this end, the body 100 includes a side portion 110 including a first side frame 111 and a second side frame 113 which is spaced apart from the first side frame 111, and a bridge 120 which connects the first side frame 111 and the second side frame 113 to each other.

The side portion 110 may fix the bridge 120 on both sides to provide a sense of stability when the body 100 is mounted on the head of the subject.

A plurality of bridges 120 may be provided and may be spaced apart from each other in a front-rear direction. In other words, the bridges 120 may include a first bridge 120a, a second bridge 120b, a third bridge 120c, a fourth bridge 120d, and a fifth bridge 120e spaced apart from each other from the front to the rear. Of course, the bridge 120 may be formed as a single unit or may be provided in a plurality of six or more. However, it is preferable that five bridges 120 are provided under the above-described 10-20 system.

When the plurality of bridges 120 are provided, the side portion 110 may include branch portions for supporting the plurality of bridges 120 at both ends.

Specifically, the first side frame 111 may include a first side body 1111 and a plurality of first branch portions 1113 which are branched off from the first side body 1111. The first branch portions 1113 may be provided in plural (1113a to 1113e) and may be spaced apart from each other and coupled to a plurality of first adjustment housings 410 to be described later, respectively.

Similarly, the second side frame 113 may include a second side body 1131 and a plurality of second branch portions 1133 which are branched from the second side body 1131. The second branch portions 1133 may be provided in plural (1133a to 1133e) and may be spaced apart from each other and coupled to the plurality of first adjustment housings 410 to be described later, respectively.

In other words, the first branch portion 1113 may be coupled to one end of the bridge 120, and the second branch portion 1133 may be coupled to the other end of the bridge 120.

The adjuster 400 may be provided in the bridge 120 to adjust the size of the bridge 120.

To this end, each of the plurality of bridges 120 may be provided with a plurality of frames or housings. In this case, the adjuster 400 may be provided between the plurality of frames or housings and may move the frame or housing in a direction moving away or closer to the frame or housing based on the adjuster 400. Each of the plurality of frames or housings may be referred to as a bridge frame or a bridge housing. The bridge housing may be constituted by a plurality of types of housings.

Accordingly, at least one adjuster 400 may be provided in each of the plurality of bridges 120 so that the size of the body 100 can be flexibly adjusted.

Meanwhile, the sensing unit 200 may be defined as a configuration which detects an electrical signal generated from a portion of the head of the subject. In this case, it is preferable that a plurality of sensing units 200 are provided. As described above, in the case of the 10-20 system, at least 19 electrode channels are required, and as the number of the sensing units 200 increases, a reliable EEG can be measured.

However, even if the plurality of sensing units 200 are provided, the overall configuration of each of the sensing units 200 may be the same as each other.

Hereinafter, the sensing unit 200 according to one exemplary embodiment of the present disclosure will be described with reference to FIGS. 3A and 3B.

Figure 3A:
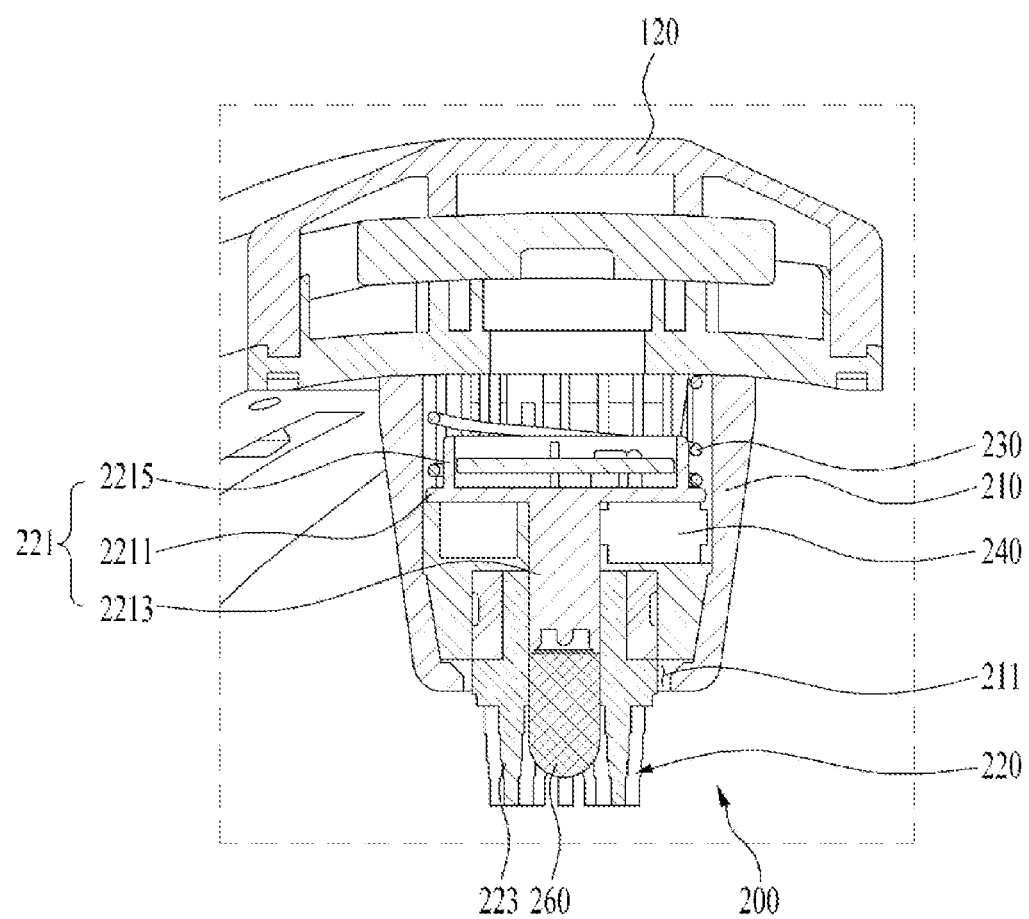
FIGS. 3A and 3B are views illustrating a sensing unit according to one exemplary embodiment of the present disclosure.
Figure 3B:
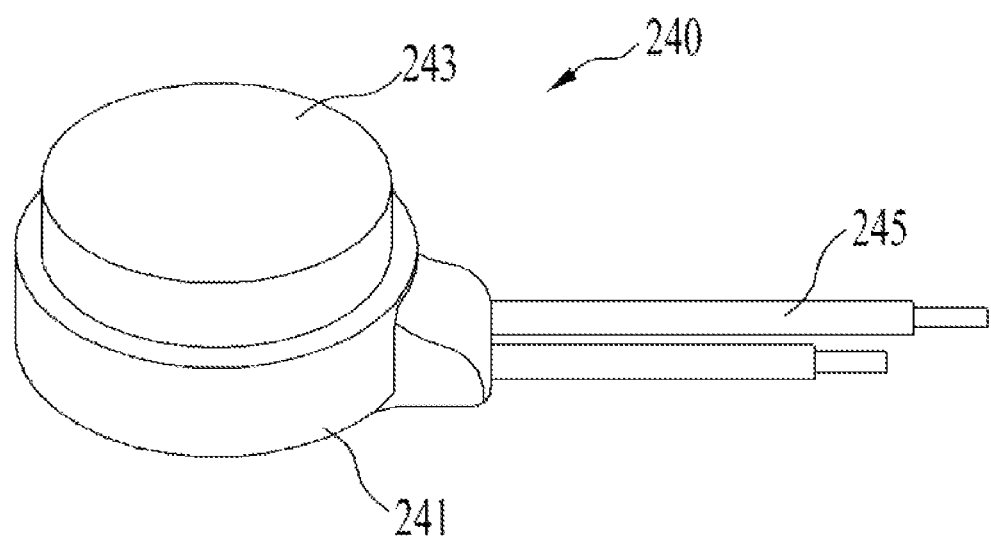

FIG. 3A is a cross-sectional view of the sensing unit 200 according to one exemplary embodiment of the present disclosure, and FIG. 3B is a view illustrating a vibrator 240 according to one exemplary embodiment of the present disclosure.

The sensing unit 200 includes a sensor housing 210 and an electrode unit 220, which is provided to come into contact with the head of the subject, inside the sensor housing 210.

The sensor housing 210 may be provided on an inner peripheral surface of the body 100. Meanwhile, the inner peripheral surface of the body 100 may be defined as a surface facing the head of the subject.

Specifically, the sensor housing 210 may be provided in at least one of the side portion 110 and the bridge 120. For example, the sensor housing 210 may be provided in each of the first side frame 111 and the second side frame 113, and may be provided on the inner peripheral surface of the bridge 120.

However, since the plurality of sensing units 200 are provided, the sensor housing 210 may also be provided in the adjuster 400.

One side of the sensor housing 210 is provided on the inner peripheral surface of the body 100 or on the adjuster 400 and an opening 211 is formed on the other side of the sensor housing 210.

The electrode unit 220 is provided inside the sensor housing 210, and may protrude to the outside of the sensor housing 210 through the opening 211. In other words, a portion of the electrode unit 220 may be located inside the sensor housing 210 and the rest of the electrode unit 220 may be located outside the sensor housing 210.

The electrode unit 220 may include an electrode housing 221 which is provided inside the sensor housing 210, and an electrode 223 which is provided in the electrode housing 221 and exposed to the outside of the sensor housing 210 through the opening 211.

The electrode housing 221 may include a disk frame 2211 which is spaced apart from the electrode 223, a first protrusion 2213 which protrudes from the disk frame 2211 and is coupled to the electrode 223, and a second protrusion 2215 which protrudes from the disk frame 2211 in a direction away from the electrode 223.

The electrode 223 is configured to come into contact with the head of the subject to detect the electrical signal generated from the head of the subject, and may be provided in plural. When the plurality of electrodes 223 are provided, a plurality of electrodes may be provided to surround the first protrusion 2213.

However, the electrode 223 may be provided as a single electrode and may have a cylindrical shape of which a contact surface with the head of the subject is flat.

In addition, the electrode 223 may be coated with silver (Ag) or silver chloride (AgCl) regardless of the shape of the electrode 223.

Accordingly, when the body 100 is mounted on the head of the subject, the sensing unit 200 may detect the electrical signal generated from the head of the subject, and the detected electrical signal may be transmitted to the controller 300. In this case, the sensing unit 200 may further include a printed circuit board (PCB) 250 which transmits the electrical signal detected by the electrode unit 220 to the controller 300 or directly converts the electrical signal into an EEG signal. The PCB 250 may supply power to the electrode unit 220.

However, the body 100 may not be in close contact with the head of the subject or may be difficult to maintain close contact due to hair of the subject.

To this end, the sensing unit 200 may further include at least one of an elastic member 230 which is provided inside the sensor housing 210 to provide an elastic force to the electrode unit 220, and a vibrator 240 which is provided inside the sensor housing 210 to provide vibrations to the electrode unit 220.

The elastic member 230 may be provided between one side of the sensor housing 210 and the electrode unit 220 to provide the elastic force to the electrode unit 220. Specifically, one end of the elastic member 230 may be provided on the disk frame 2211 and the other end thereof may be provided on one side of the sensor housing 210. In this case, the elastic member 230 may be provided to surround the second protrusion 2215.

The elastic member 230 is not limited as long as it has a shape capable of providing an elastic force. For example, a coil-spring may be provided as the elastic member 230.

Accordingly, when the electrode unit 220 comes into contact with the head of the subject, the resistance felt by the subject may be reduced. In addition, after the subject wears the body 100, an effect of the body 100 continuously in close contact with the head of the subject can be expected.

The vibrator 240 may include a vibration frame 241, a vibration member 243 which is disposed on one side of the vibration frame 241 and vibrates, and a vibration power supply 245 which supplies power to the vibration member 243.

The vibration power supply 245 may receive power from the PCB 250 or the controller 300 and transmit the power to the vibration member 243.

Preferably, the vibrator 240 is provided adjacent to the electrode unit 220 to transmit vibrations to the electrode unit 220. More preferably, the vibrator 240 may be provided between the elastic member 230 and the electrode 223. This is because a change in position of the electrode unit 220 by the elastic member 230 is larger than a change in position of the electrode unit 220 by the vibrator 240.

Thus, when the body 100 is mounted on the head of the subject, the elastic member 230 can primarily bring the body 100 into close contact with the head of the subject, and the vibrator 240 can minimize an intermittent separation between the head of the subject and the body 100.

Meanwhile, the sensing unit 200 may further include a light emitting diode (LED) 260 which is provided in the electrode unit 220 and emits infrared rays (preferably near infrared rays). The LED 260 may be provided to be surrounded by the plurality of electrodes 223.

Hereinafter, the controller 300 according to one exemplary embodiment of the present disclosure will be described with reference to FIG. 4.

Figure 4:
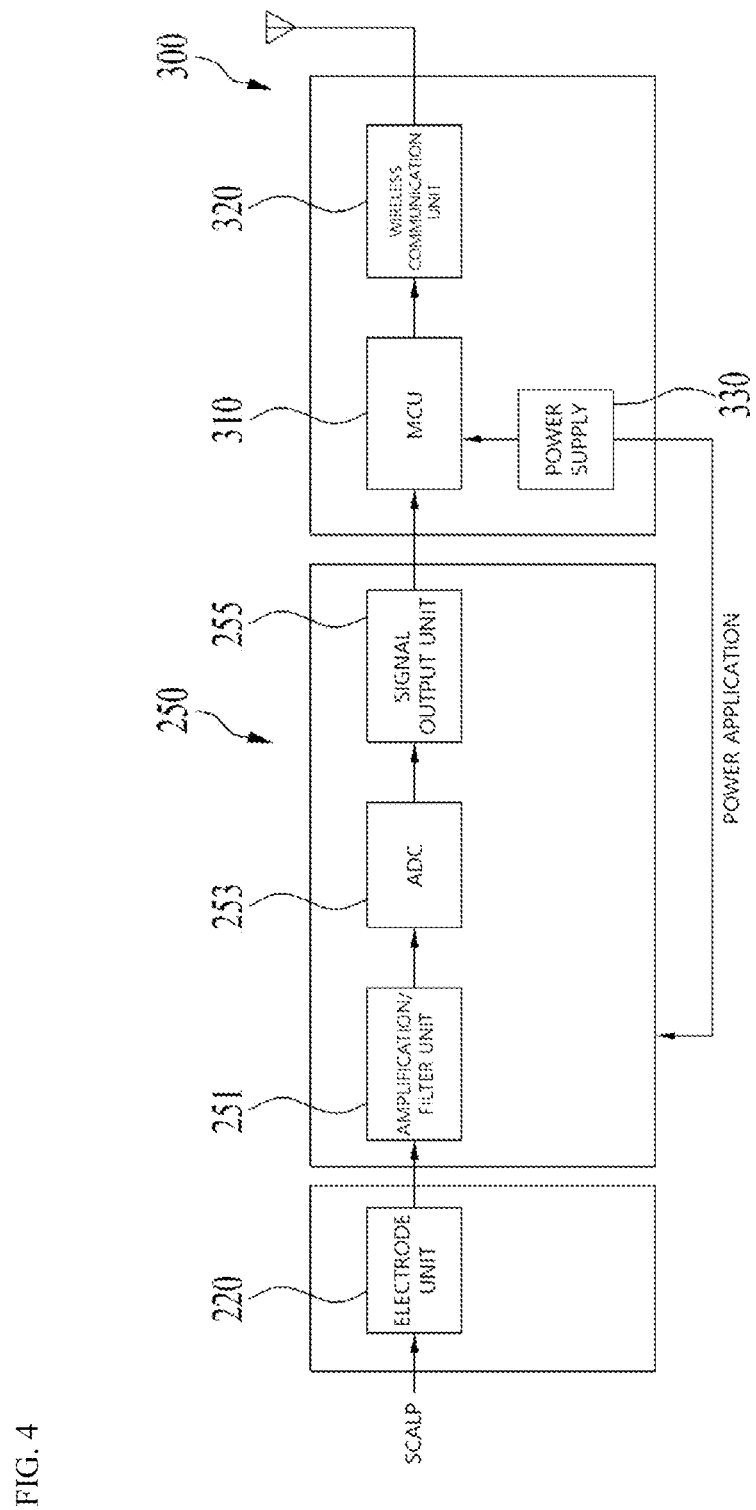
FIG. 4 is a conceptual diagram of a controller according to one exemplary embodiment of the present disclosure.

FIG. 4 is a conceptual diagram of the controller 300 according to one exemplary embodiment of the present disclosure.

The controller 300 may be provided in a separate configuration, and may be provided on the PCB 250. In other words, the PCB 250 may be equipped with functions of the controller 300 to be described later, but the PCB 250 and the controller 300 may be separated from each other to exchange information with each other.

The PCB 250 may include an amplification/filter unit 251 which receives an electrical signal from the electrode unit 220 and filters or amplifies this electrical signal, an analog-digital converter (ADC) 253 which converts the information processed by the amplification/filter unit 251 into digital information, and a signal output unit 255 which transmits the digital information converted by the ADC 253 to the controller 300.

The controller 300 may include a microprocessor (MCU) 310 which receives the information from the signal output unit 255 and converts the information into an EEG signal by a stored algorithm, a wireless communication unit 320 which receives the EEG signal from the microprocessor 310 to transmit the EEG signal to an external device (a mobile device or the like), and a power supply 330 which supplies power to the PCB 250 and the microprocessor 310.

However, as described above, the amplification/filter unit 251, the ADC 253, and the signal output unit 255 may all be provided in the controller 300.

Accordingly, the electrical signal generated from the head of the subject may be converted into the EEG signal and provided to the external device, and the user may check EEG information of the subject through the external device.

Meanwhile, apart from the body 100 being in close contact with the head of the subject, a size of the head of the subject varies. In other words, when the size of the body 100 is constant, there is a problem that it is difficult to mount the body 100 on a head of a specific subject, or it is difficult to trust the measured EEG signal.

Hereinafter, the adjuster 400 for solving the above problem will be described with reference to FIGS. 5A to 7B.

Figure 5A:
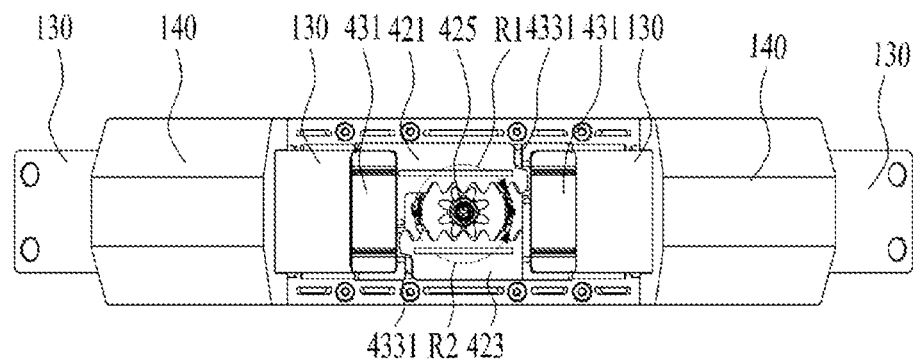
FIGS. 5A and 5B are views illustrating an adjuster when the size of the EEG measuring device according to one exemplary embodiment of the present disclosure is minimum.
Figure 5B:
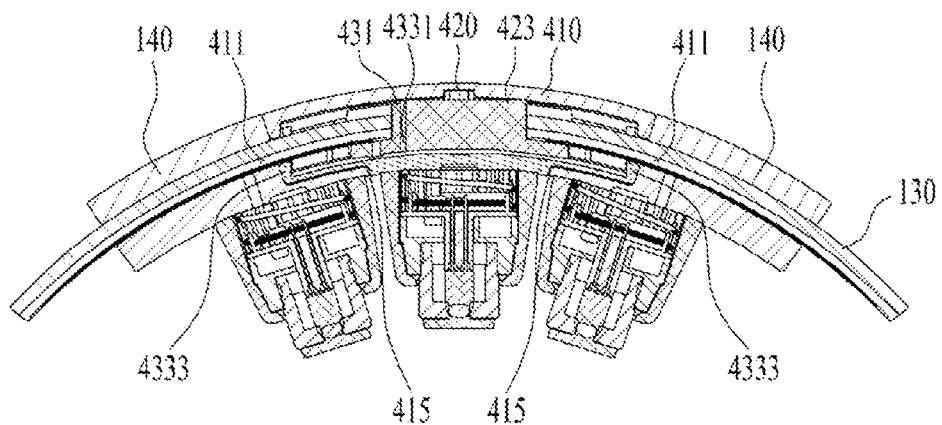

FIG. 5A is a view when the adjuster is viewed from above in a case in which a size of the EEG measuring device according to one exemplary embodiment of the present disclosure is minimum, and FIG. 5B is a cross-sectional view of the adjuster when the size of the EEG measuring device is minimum.

Figure 6A:
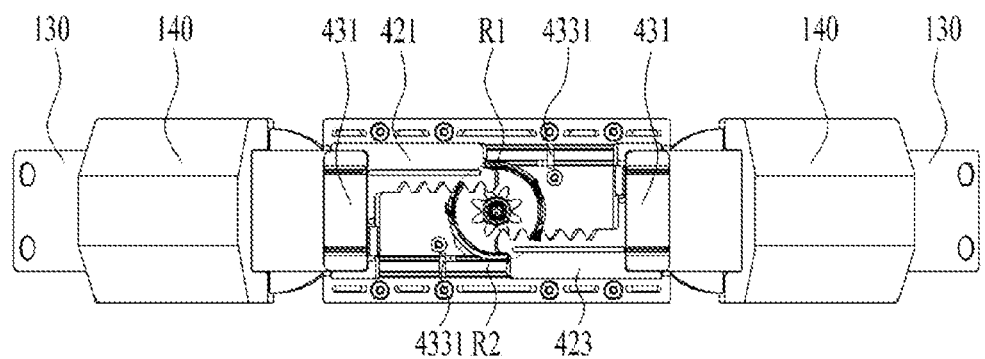
FIGS. 6A and 6B are views illustrating the adjuster when the size of the EEG measuring device according to one exemplary embodiment of the present disclosure is maximum.
Figure 6B:
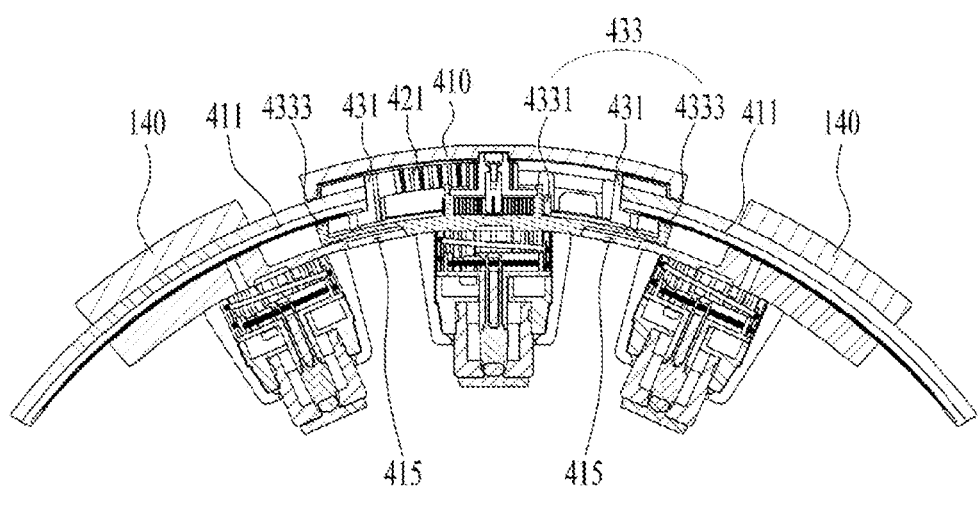

FIG. 6A is a view when the adjuster is viewed from above in a case in which the size of the EEG measuring device according to one exemplary embodiment of the present disclosure is maximum, FIG. 6B is a cross-sectional view of the adjuster when the size of the EEG measuring device is maximum.

Figure 7A:
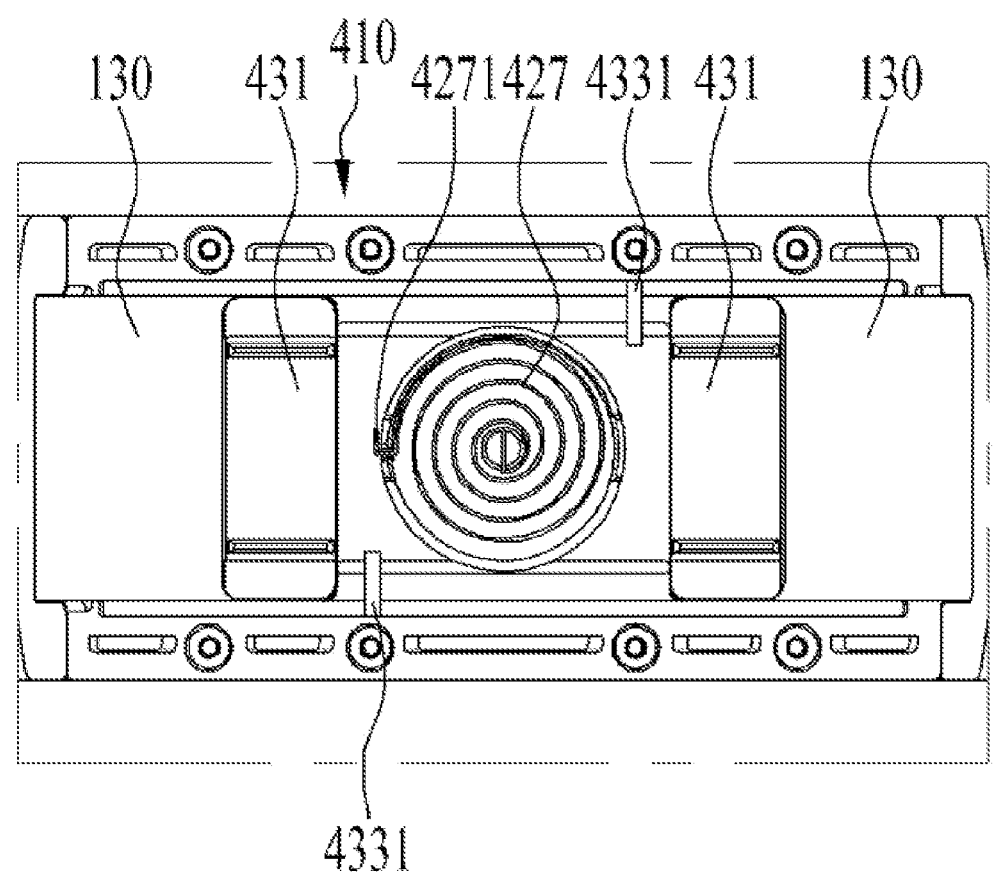
FIGS. 7A and 7B are views illustrating an adjustment elastic member according to one exemplary embodiment of the present disclosure.
Figure 7B:
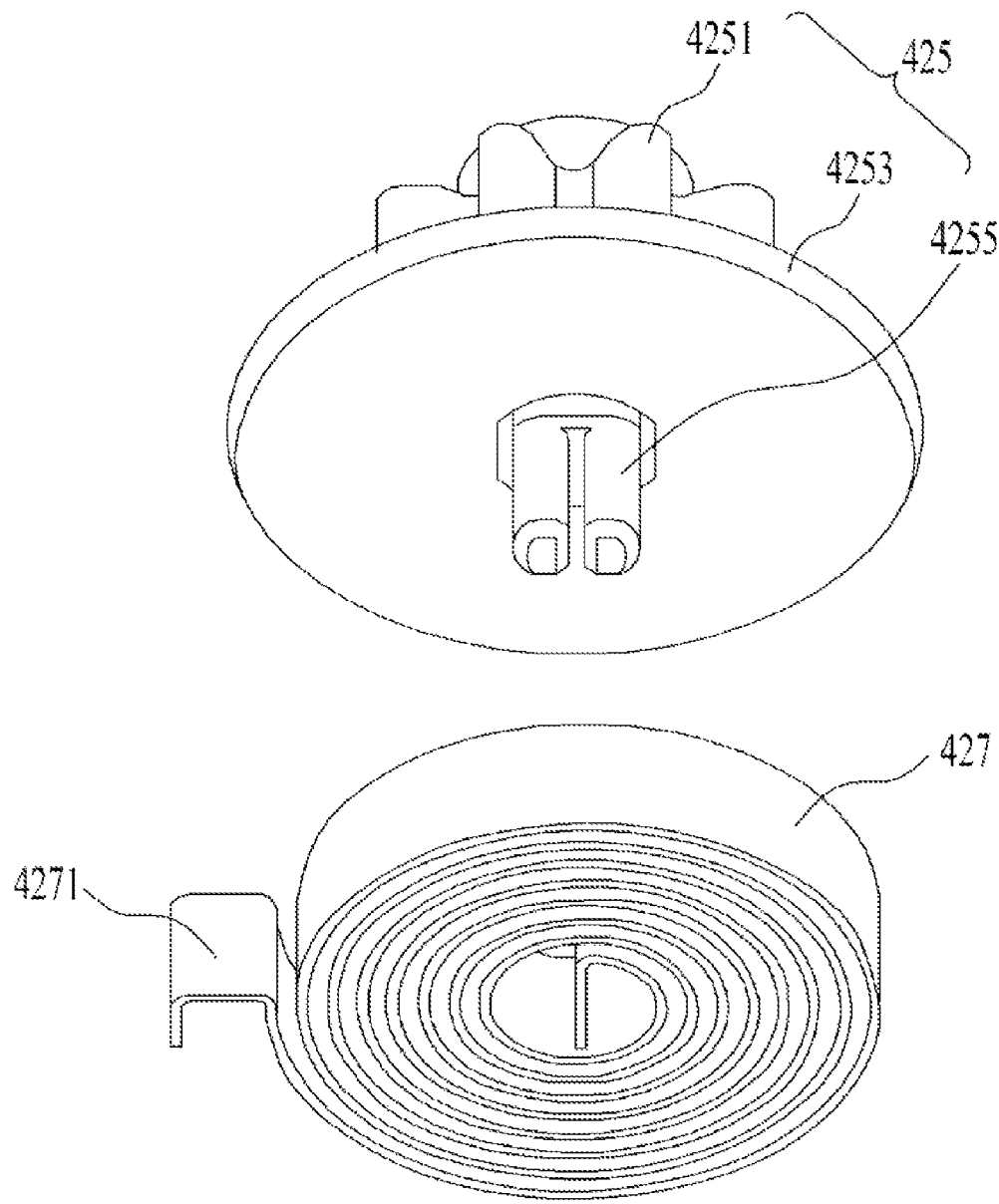

FIG. 7A is a view illustrating a state in which an adjustment elastic member is provided in the adjuster according to one exemplary embodiment of the present disclosure, and FIG. 7B is a view illustrating the adjustment elastic member.

Referring to FIGS. 5A to 6B, the adjuster 400 may include an adjustment housing 410 and a symmetrical mover 420 which is provided inside the adjustment housing 410 to move the bridge 120 closer to or away from the adjustment housing 410. The adjustment housing 410 is a configuration formed in the bridge housing, and in some cases, the adjustment housing 410 and the bridge housing may be defined as the same configuration.

In this case, the bridge 120 may further include a connection frame 130 for connecting the adjustment housing 410 to the side portion 110.

The connection frame 130 may connect the inner side of the adjustment housing 410 and one of the first side frame 111 and the second side frame 113 to each other, and may connect the inner side of the adjustment housing 410 and the other of the first side frame 111 and the second side frame 113 to each other. In other words, the connection frame 130 may connect one side of the adjustment housing 410 and the side portion 110 to each other and may connect the other side of the adjustment housing 410 and the side portion 110 to each other.

That is, the connection frame 130 may not be provided as a single frame, but may be provided as a plurality of frames.

Meanwhile, the connection frame 130 may be made of a material having elasticity, and may have an elastic force so that the connection frame 130 may be slightly twisted according to a head shape and a head size of a user.

A space in which the connection frame 130 can move may be formed in the adjustment housing 410. As will be described later, the connection frame 130 may be movable inside the adjustment housing 410 at each of both sides of the adjustment housing 410. Accordingly, the adjustment housing 410 may include a connection guide which is provided in the adjustment housing 410 and guides a movement of the connection frame 130.

The symmetrical mover 420 may include a first connection rack gear 421 which connects one side of the adjustment housing 410 and the connection frame 130 to each other, a second connection rack gear 423 which connects the other side of the adjustment housing 410 and the connection frame 130 to each other and is spaced apart from the first connection rack gear 421, and a connection pinion gear 425 which is provided to engage with each of the first connection rack gear 421 and the second connection rack gear 423.

The first connection rack gear 421 may connect one of the frames constituting the connection frame 130 to the inner side of the adjustment housing 410, and the second connection rack gear 423 may connect the other of the frames constituting the connection frame 130 to the inner side of the adjustment housing 410.

Accordingly, when the connection pinion gear 425 rotates in a first direction R1, the connection frames 130 located at both sides of the adjustment housing 410 may move in a direction closer to each other, and when the connection pinion gear 425 rotates in a second direction R2, the connection frames 130 located at both sides of the adjustment housing 410 may move in a direction further away from each other.

Here, the first direction R1 may be defined as a forward direction or the clockwise direction, and the second direction R2 may be defined as a reverse direction or the counterclockwise direction (with reference to the drawings).

Therefore, when the connection pinion gear 425 rotates in the forward direction, the first connection rack gear 421 and the second connection rack gear 423 may move to be closer to each other, and when the connection pinion gear 425 rotates in the reverse direction, the first connection rack gear 421 and the second connection rack gear 423 may move away from each other.

However, when the connection pinion gear 425 is continuously rotated in the forward or reverse direction, there is a problem that the first connection rack gear 421 and the second connection rack gear 423 collide with each other or are separated from the inside of the adjustment housing 410.

In order to solve the problem, the adjuster 400 may further include a stopper which limits the rotation of the connection pinion gear 425.

The stopper may include a protruding member 433 provided to come into contact with the first connection rack gear 421 and the second connection rack gear 423.

The protruding member 433 includes a first protruding member 4331 which is provided to be able to come into contact with each of a surface (first surface) in which the first connection rack gear 421 faces the second connection rack gear 423 and a surface (first surface) in which the second connection rack gear 423 faces the first connection rack gear 421, and a second protruding member 4333 which is provided to be able to come into contact with each of the other surface (second surface) of the first connection rack gear 421 and the other surface (second surface) of the second connection rack gear 423.

The first protruding member 4331 is a configuration which limits a maximum moving distance in the direction in which movable housings 140 at both ends move closer to the adjuster 400 by the rotation of the connection pinion gear 425, and the second protruding member 4333 is a configuration which limits a maximum moving distance in a direction in which the movable housings 140 at both ends move away from the adjuster 400 by the rotation of the connection pinion gear 425 in the reverse direction. One or two or more movable housings 140 may be provided for each bridge depending on the type of bridge.

The first protruding member 4331 may limit the rotation of the connection pinion gear 425 in the forward direction, and the second protruding member 4333 may limit the rotation of the connection pinion gear 425 in the reverse direction.

The first protruding member 4331 may be provided inside the adjustment housing 410 and may be provided adjacent to the connection pinion gear 425. In addition, the first protruding member 4331 may be provided in plural, and may be provided to be in contact with the first connection rack gear 421 or the second connection rack gear 423.

The second protruding member 4333 may be provided inside the adjustment housing 410 and may be located farther from the connection pinion gear 425 than the first protruding member 4331. In this case, the second protruding member 4333 may be a portion of the adjustment housing 410. More specifically, openings 411 through which the connection frame 130 can move may be formed at both sides of the adjustment housing 410. In this case, the second protruding member 4333 may be in contact with a portion of both side surfaces of the adjustment housing 410 except for the openings 411.

Accordingly, the symmetrical mover 420 may change the size of the bridge 120, and may eventually change the size of the body 100. Therefore, even when the size of the head of the subject varies, the body 100 may be mounted on the head of the subject by the symmetrical mover 420.

However, even when the body 100 is mounted on the head of the subject, there is a need to bring the body 100 into close contact with the head of the subject. In other words, even when the body 100 is mounted on the head of the subject, if a close contact is not maintained, it may be difficult to generate a reliable EEG signal.

Of course, as described above, the sensing unit 200 may include the configuration (that is, the elastic member or the vibrator) for the close contact. However, this is a configuration which allows the electrode unit 220 to come into close contact with the head of the subject within the size limit of the body 100.

Therefore, it is necessary to bring the body 100 itself into close contact with the head of the subject without being limited to the electrode unit 220.

Referring to FIGS. 7A and 7B, the symmetrical mover 420 may further include an adjustment elastic member 427 which is coupled to the connection pinion gear 425 to bring the body 100 into close contact with the head of the subject.

The adjustment elastic member 427 is configured to provide a restoring force to the body 100. In other words, the adjustment elastic member 427 may be defined as a configuration which returns the size of the body 100 to the size before the size of the body 100 is changed when the body 100 becomes larger than a predetermined size.

The adjustment elastic member 427 may be provided as a spiral spring or a flat spring.

FIGS. 7A and 7B illustrate a case in which the adjustment elastic member 427 is provided as a spiral spring, but there is no significant limitation on the shape of the adjustment elastic member 427 as long as it can provide a restoring force.

The adjustment elastic member 427 may be coupled to the connection pinion gear 425 to provide a restoring force to the connection pinion gear 425. To this end, the connection pinion gear 425 may include a pinion housing 4253, a gear 4251 which is coupled to one side of the pinion housing 4253 to engage with the connection rack gears 421 and 423, and a fastener 4255 which is coupled to the other side of the pinion housing 4253 to couple with the adjustment elastic member 427.

The fastener 4255 may be configured to form a rotary shaft of the gear 4251 and provide displacement to the adjustment elastic member 427.

Specifically, when the connection pinion gear 425 is rotated by the connection rack gears 421 and 423, the fastener 4255 which is the rotary shaft of the connection pinion gear 425 rotates together with the connection pinion gear 425. In this case, the rotated fastener 4255 rotates the adjustment elastic member 427, and the rotated adjustment elastic member 427 may provide a restoring force.

In this case, the adjustment elastic member 427 may include a fixing portion 4271 fixed to the adjustment housing 410. As the fixing portion 4271 is fixed to the adjustment housing 410, the adjustment elastic member 427 may provide a restoring force to the connection pinion gear 425.

Accordingly, when the connection pinion gear 425 rotates in the reverse direction, the adjustment elastic member 427 may provide a restoring force to the connection pinion gear 425 to rotate the connection pinion gear 425 in the forward direction.

Accordingly, the adjuster 400 may provide a restoring force to the body 100 so that the body 100 comes into close contact with the head of the subject while changing the size of the body 100.

Meanwhile, as the size of the body 100 is changed, the position of each of the plurality of sensing units 200 may be important. This is because the change in the size of the body 100 may change the position of the sensing unit 200, and the change in the position of the sensing unit 200 may decrease reliability of the EEG signal.

To this end, according to the exemplary embodiment of the present disclosure, the sensing unit 200 may be disposed by classifying the bridge 120 into two types.

Hereinafter, two types of bridges 120 will be described with reference to FIGS. 1A to 2C, 5A to 6B, and 8A to 9B.

Figure 8A:
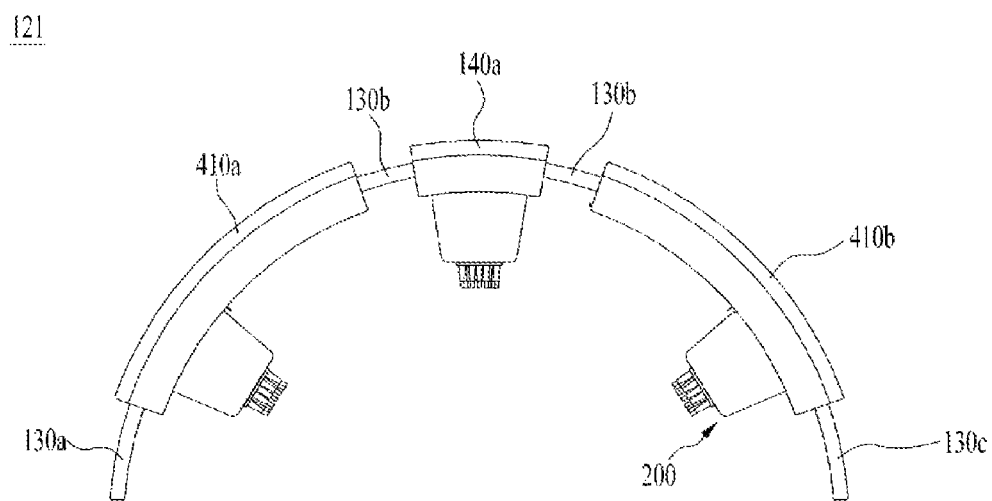
FIGS. 8A and 8B are views illustrating a first type bridge according to one exemplary embodiment of the present disclosure.
Figure 8B:
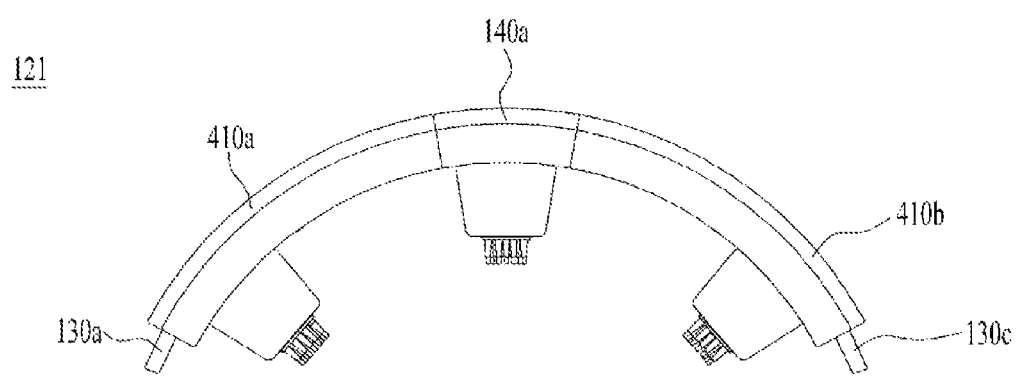
Figure 9A:
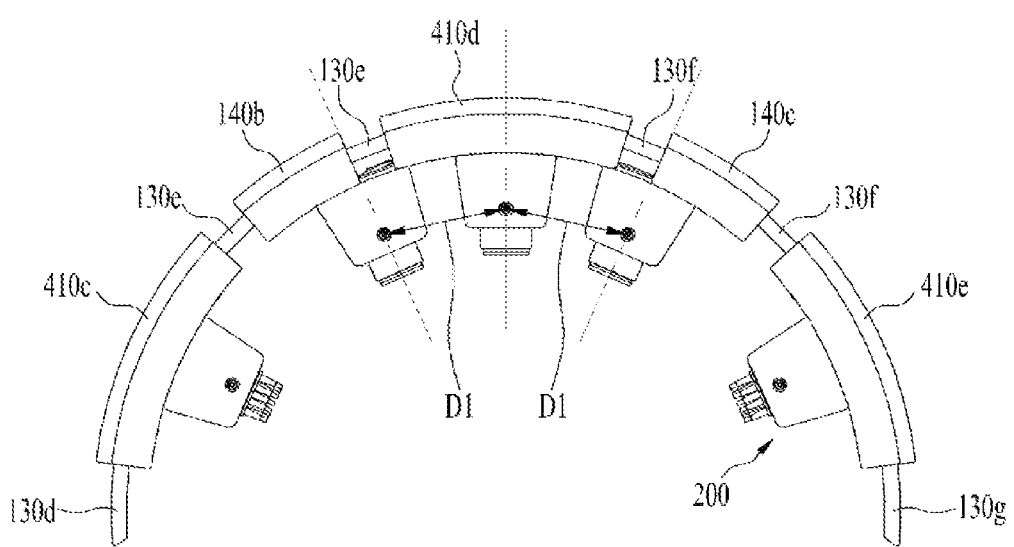
FIGS. 9A and 9B are views illustrating a second type bridge according to one exemplary embodiment of the present disclosure.
Figure 9B:
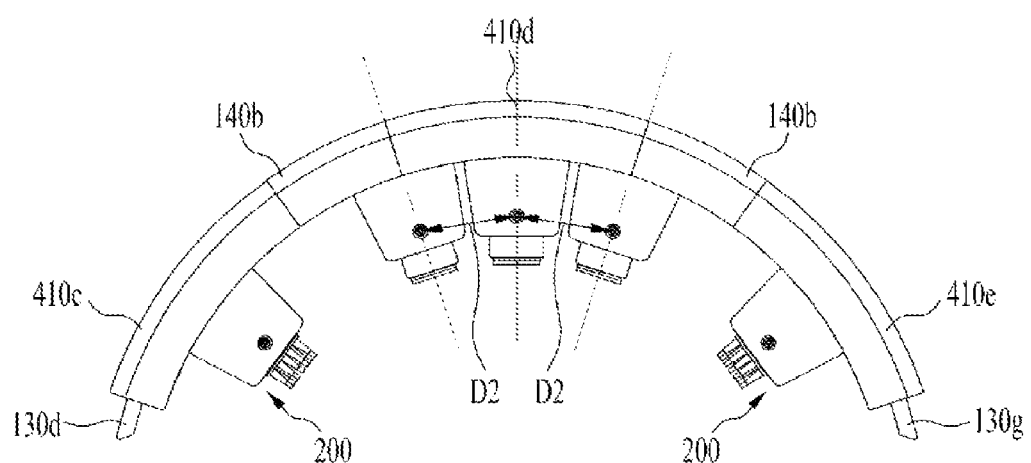

FIGS. 8A and 8B are views illustrating a first type bridge according to one exemplary embodiment of the present disclosure, and FIGS. 9A and 9B are views illustrating a second type bridge according to one exemplary embodiment of the present disclosure. The adjustment housing may be interpreted as a portion of the bridge housing or may be described as the same concept as the bridge housing.

The first type bridge 121 may include two adjustment housings 410 and three connection frames 130.

Each of the first type bridge 121 and the second type bridge 123 may include a movable housing 140. The movable housing 140 is provided to be movable with respect to the adjustment housing 410, and the sensing unit 200 may be coupled to the movable housing 140.

The connection frame 130 may be fixed to the movable housing 140 to move together with the movable housing 140.

That is, the adjuster 400 may move the connection frames 130 disposed at both sides based on the adjustment housing 410, and the movable housing 140 may be fixed to the connection frame 130 and may move simultaneously with the connection frame 130.

Accordingly, the sensing unit 200 coupled to the movable housing 140 may move away from or closer to the adjustment housing 410.

Specifically, the adjustment housing 410 may include a first first-type adjustment housing 410a and a second first-type adjustment housing 410b spaced apart from the first first-type adjustment housing 410a.

The bridge 120 may include a first movable housing 140a provided between the first first-type adjustment housing 410a and the second first-type adjustment housing 410b.

The connection frame 130 may include a first first-type connection frame 130a which connects any one of the first side frame 111 and the second side frame 113 and the first first-type adjustment housing 410a to each other, a second first-type connection frame 130b which connects the first first-type adjustment housing 410a and the second first-type adjustment housing 410b to each other and passes through the first movable housing 140a, and a third first-type connection frame 130c which connects the second first-type adjustment housing 410b and the other of the first side frame 111 and the second side frame 113 to each other.

The first type bridge 121 may include the first first-type adjustment housing 410a, the second first-type adjustment housing 410b, the first movable housing 140a, the first first-type connection frame 130a, the second first-type connection frame 130b, and the third first-type connection frame 130c.

Unlike the above, the second type adjustment housing 410 illustrated in FIGS. 9A and 9B may include a first second-type adjustment housing 410c, a second second-type adjustment housing 410d, and a third second-type adjustment housing 410e spaced apart from each other.

The bridge 120 may include a first second-type movable housing 140b which is provided between the first second-type adjustment housing 410c and the second second-type adjustment housing 410d, and a second second-type movable housing 140c which is provided between the second second-type adjustment housing 410d and the third second-type adjustment housing 410e.

The connection frame 130 may include a first second-type connection frame 130d which connects any one of the first side frame 111 and the second side frame 113 and the first second-type adjustment housing 410c to each other, a second second-type connection frame 130e which connects the first second-type adjustment housing 410c and the second second-type adjustment housing 410d and passes through the first second-type movable housing 140b, a third second-type connection frame 130f which connects the second second-type adjustment housing 410d and the third second-type adjustment housing 410e and passes through the second second-type movable housing 140c, and a fourth second-type connection frame 130g which connects the third second-type adjustment housing 410e and the other of the first side frame 111 and the second side frame 113 to each other.

The second type bridge 123 may include the first second-type adjustment housing 410c, the second second-type adjustment housing 410d, the third second-type adjustment housing 410e, the first second-type movable housing 140b, the second second-type movable housing 140c, the first second-type connection frame 130d, the second second-type connection frame 130e, the third second-type connection frame 130f, and the fourth second-type connection frame 130g.

The reason that the bridge 120 is classified into the first type bridge 121 and the second type bridge 123 is to allow the body 100 to be more smoothly mounted on the head of the subject. Therefore, when five bridges are provided, it is preferable that some of the five bridges are provided as the first type bridges 121 and the remaining bridges are provided as the second type bridges 123.

Preferably, the first bridge 120a and the fifth bridge 120e may be provided as the second type bridges 123, and the second to fourth bridges 120b to 120d may be provided as the first type bridges 121. This is due to the fact that portions of the head of the subject having various sizes are the forehead and the back of the head. In this case, first, the second to fourth bridges 120b to 120d are mounted on the head of the subject, and then the first and fifth bridges 120a and 120e may be adjusted so that the EEG measuring device comes into close contact with the head of the subject.

Accordingly, the sensing units 200 which are respectively provided in the side portion 110, the adjustment housing 410, and the movable housing 140 can measure a reliable EEG signal from the head of the subject.

Hereinafter, a configuration for detecting a reliable EEG signal will be described.

In the case of the first type bridge 121, preferably, the sensing unit 200 provided in the movable housing 140 is located at a center of one surface facing the head of the subject among the surfaces forming the first movable housing 140a. In addition, preferably, the first first-type adjustment housing 410a and second first-type adjustment housing 410b respectively located at both sides based on the first movable housing 140a have the same shape and are symmetrical to each other based on the first movable housing 140a.

In the case of the second type bridge 123, preferably, the sensing unit 200 provided in the second second-type adjustment housing 410d is located at a center of one surface facing the head of the subject among the surfaces forming the second second-type adjustment housing 410d.

Preferably, the first second-type movable housing 140b and the second second-type movable housing 140c have the same shape and are symmetrical to each other based on the second second-type adjustment housing 140d.

Preferably, the first second-type adjustment housing 410c and the third second-type adjustment housing 410e have the same shape and are symmetrical to each other based on the second second-type adjustment housing 410d.

In addition, preferably, the sensing unit 200 provided in the first second-type movable housing 140b and the sensing unit 200 provided in the second second-type movable housing 140c are symmetrical based on the sensing unit 200 provided in the second second-type adjustment housing 410d. Accordingly, distances D1 and D2 between the sensing unit 200 provided in the second second-type adjustment housing 410d and the sensing unit 200 provided in the first second-type movable housing 140b may be equal to distances D1 and D2 between the sensing unit 200 provided in the second second-type adjustment housing 410d and the sensing unit 200 provided in the second second-type movable housing 140c.

Meanwhile, the first second-type movable housing 140b may include a first extension extending toward the second second-type adjustment housing 410d from one surface facing the head of the subject, and the sensing unit 200 may be coupled to the first extension.

Similarly, the second second-type movable housing 140c may include a second extension extending toward the second second-type adjustment housing 140d from one surface facing the head of the subject, and the sensing unit 200 may be coupled to the second extension.

In the above case, the second second-type adjustment housing 410d may have a recess 415 which is formed concave to accommodate the first extension and the second extension on one surface facing the head of the subject.

According to the exemplary embodiment of the present disclosure, it is possible to efficiently measure an EEG irrespective of differences in head shapes and head sizes.

According to the exemplary embodiment of the present disclosure, it is possible to provide an EEG measuring device whose size is changed.

According to the exemplary embodiment of the present disclosure, it is possible to provide an EEG measuring device having a large size change range at the forehead and the back of the head of a subject.

According to the exemplary embodiment of the present disclosure, even when the size of the device is changed according to a head shape, it is possible to provide an EEG measuring device which reliably measures the EEG According to the exemplary embodiment of the present disclosure, even if the size of the device is changed according to a head shape, it is possible to provide an EEG measuring device which is in close contact with a head of a subject.

It will be apparent to those skilled in the art that various modifications can be made to the above-described exemplary embodiments of the present disclosure without departing from the spirit or scope of the invention. Thus, it is intended that the present disclosure covers all such modifications provided they come within the scope of the appended claims and their equivalents.

What is claimed is:

1. An electroencephalogram (EEG) measuring device comprising:
 a body configured to be mounted at a head of a subject;
 a sensor provided at the body and configured to detect an electrical signal generated from the head;

a controller configured to supply power to the sensor and convert the electrical signal detected by the sensor into an EEG signal; and a plurality of adjusters provided at the body and configured to adjust a size of the body, wherein the body includes a plurality of segments that are connected to each other and are movable relative to each other, and wherein each adjuster of the plurality of adjusters is configured to bias a respective segment of the plurality of segments toward an adjacent segment of the plurality of segments.

2. The EEG measuring device of claim 1, wherein the body comprises:

side portions including a first side frame and a second side frame that is spaced apart from the first side frame and opposite to the first side frame, and a plurality of bridges connecting the first side frame to the second side frame, wherein each of the plurality of bridges comprises a plurality of bridge housings, at least one movable housing connected to one or more of the plurality of bridge housings and configured to move with respect to one or more of the plurality of bridge housings, and a plurality of connection frames connecting one or more of the plurality of bridge housings to the side portions or connecting the plurality of bridge housings to the at least one movable housing, and wherein each adjuster of the plurality of adjusters is provided at a respective one of the plurality of bridges.

3. The EEG measuring device of claim 2, wherein the plurality of connection frames each include a first connection frame and a second connection frame, wherein each of the plurality of adjusters comprises:

an adjustment housing, and a symmetrical mover provided inside the adjustment housing and configured to move a corresponding first connection frame and a corresponding second connection frame, the first connection frame being connected to a first end of the adjustment housing, and the second connection frame being connected to a second end of the adjustment housing being opposite to the first end of the adjustment housing.

4. The EEG measuring device of claim 3, wherein each symmetrical mover comprises:

a first connection rack gear connecting a first side of a corresponding adjustment housing to the corresponding first connection frame, a second connection rack gear connecting a second side of the corresponding adjustment housing to the corresponding second connection frame and being spaced apart from the first connection rack gear, and a connection pinion gear configured to engage with each of the first connection rack gear and the second connection rack gear, and wherein the first connection rack gear and the second connection rack gear are positioned to face each other.

5. The EEG measuring device of claim 4, wherein each symmetrical mover further comprises:

an adjustment elastic member coupled to the connection pinion gear and configured to, based on the connection pinion gear rotating in a first rotational direction, apply a restoring force to the connection pinion gear in a second rotational direction opposite to the first rotational direction.

6. The EEG measuring device of claim 3, wherein a first bridge housing of the plurality of bridge housings in one of the plurality of bridges is connected to the first side frame, wherein a second bridge housing of the plurality of bridge housings in the of the plurality of bridges is connected to the second side frame, and wherein the at least one moveable housing in the one of the plurality of bridges comprises a first movable housing connecting the first bridge housing to the second bridge housing.

7. The EEG measuring device of claim 3, wherein a first bridge housing of the plurality of bridge housings in one of the plurality of bridges is connected to the first side frame, wherein a second bridge housing of the plurality of bridge housings in the one of the plurality of bridges is connected to the second side frame, and wherein the at least one moveable housing in the one of the plurality of bridges comprises:

a first movable housing connecting the first bridge housing to a third bridge housing of the plurality of bridge housings in the one of the plurality of bridges, and a second movable housing connecting the second bridge housing to the third bridge housing.

8. The EEG measuring device of claim 4, wherein each adjuster further comprises a stopper configured to limit rotation of the connection pinion gear, and wherein the stopper comprises:

a first protrusion configured to contact each of a surface of the first connection rack gear and a surface of the second connection rack gear, and a second protrusion configured to contact each of a surface opposite to the surface of the first connection rack gear and a surface opposite to the surface of the second connection rack gear.

9. The EEG measuring device of claim 1, wherein the sensor comprises:

a sensor housing having a first side and a second side, the first side being coupled to an inner peripheral surface of the body, and the second side defining an opening, an electrode coupled to an inner side of the sensor housing and protruding through the opening, and an elastic member provided between the first side of the sensor housing and the electrode and configured to apply an elastic force to the electrode.

10. The EEG measuring device of claim 9, wherein the sensor further comprises:

a vibrator positioned between the electrode and the elastic member and configured to vibrate, and a light emitting diode (LED) positioned at the electrode and configured to emit infrared rays.

* * * * *